(12) United States Patent
Usuda

(10) Patent No.: US 11,324,388 B2
(45) Date of Patent: May 10, 2022

(54) ENDOSCOPE DEVICE, ENDOSCOPE OPERATION METHOD, AND PROGRAM WITH MOTION PATTERN DETECTION

(71) Applicant: FUJIFILM Corporation, Tokyo (JP)

(72) Inventor: Toshihiro Usuda, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 17/037,601

(22) Filed: Sep. 29, 2020

(65) Prior Publication Data
US 2021/0007581 A1 Jan. 14, 2021

Related U.S. Application Data

(63) Continuation of application No. PCT/JP2019/014755, filed on Apr. 3, 2019.

(30) Foreign Application Priority Data

Apr. 19, 2018 (JP) .............................. JP2018-080800

(51) Int. Cl.
*A61B 1/00* (2006.01)
*G01P 13/00* (2006.01)
(Continued)

(52) U.S. Cl.
CPC ........ *A61B 1/00039* (2013.01); *A61B 1/0669* (2013.01); *A61B 1/0676* (2013.01);
(Continued)

(58) Field of Classification Search
None
See application file for complete search history.

(56) References Cited

U.S. PATENT DOCUMENTS

| 5,836,869 A | 11/1998 | Kudo et al. |
| 2002/0118880 A1* | 8/2002 | Liu .................... G06K 9/00335 382/199 |

(Continued)

FOREIGN PATENT DOCUMENTS

| JP | 2006167139 | 6/2006 |
| JP | 2014023818 | 2/2014 |

(Continued)

OTHER PUBLICATIONS

"International Search Report (Form PCT/ISA/210) of PCT/JP2019/014755", dated Jun. 18, 2019, with English translation thereof, pp. 1-3.

(Continued)

*Primary Examiner* — Stefan Gadomski
(74) *Attorney, Agent, or Firm* — JCIPRNET

(57) ABSTRACT

An endoscope device, an endoscope operation method, and a program are provided. An endoscope device includes a motion pattern identification unit that identifies a single or plurality of motion patterns indicating a specific movement of a scope head of a scope unit, an operation storage unit that stores a single or plurality of pieces of operation information for instructing an operation of the endoscope device, and the single or plurality of motion patterns of the scope head in association with each other, an operation information acquisition unit that acquires the operation information corresponding to the motion pattern from the operation storage unit on the basis of the motion pattern identified by the motion pattern identification unit, and an operation execution unit that executes an operation corresponding to the operation information acquired by the operation information acquisition unit.

15 Claims, 11 Drawing Sheets

| 121 | 123 |
|---|---|
| MOTION PATTERN OF SCOPE HEAD | OPERATION INFORMATION |
| HORIZONTALLY SHAKING TWICE | SWITCHING LIGHT SOURCE |
| ROTATION IN OPTICAL AXIS DIRECTION OF SCOPE | CHANGING MAGNIFICATION |
| ⋮ | ⋮ |

(51) Int. Cl.
 G06K 9/00 (2006.01)
 A61B 1/06 (2006.01)
 A61B 1/04 (2006.01)

(52) U.S. Cl.
 CPC .......... G01P 13/00 (2013.01); G06K 9/00335 (2013.01); *A61B 1/0005* (2013.01); *A61B 1/00006* (2013.01); *A61B 1/042* (2013.01)

(56) References Cited

U.S. PATENT DOCUMENTS

| | | | | |
|---|---|---|---|---|
| 2010/0013812 | A1* | 1/2010 | Gu | G06F 3/0346 345/207 |
| 2013/0154929 | A1* | 6/2013 | Stopp | G06F 3/0416 345/157 |
| 2013/0324999 | A1* | 12/2013 | Price | A61B 17/320092 606/41 |
| 2015/0109196 | A1* | 4/2015 | Grass | G06F 3/014 345/156 |
| 2015/0138328 | A1 | 5/2015 | Yokohama | |
| 2015/0313446 | A1 | 11/2015 | Ogawa et al. | |
| 2015/0317830 | A1 | 11/2015 | Kihara et al. | |
| 2017/0080574 | A1* | 3/2017 | Kuroda | A61B 34/74 |
| 2017/0143442 | A1* | 5/2017 | Tesar | H04N 13/344 |
| 2017/0228104 | A1* | 8/2017 | Ziraknejad | G06F 3/04883 |
| 2018/0271603 | A1* | 9/2018 | Nir | A61B 34/25 |
| 2019/0090969 | A1* | 3/2019 | Jarc | G09B 23/30 |
| 2019/0142256 | A1* | 5/2019 | Zhao | A61B 1/00045 600/109 |

FOREIGN PATENT DOCUMENTS

| | | |
|---|---|---|
| WO | 2011070845 | 6/2011 |
| WO | 2016052175 | 4/2016 |

OTHER PUBLICATIONS

"Written Opinion of the International Searching Authourity (Form/ISA/237) of PCT/JP2019/014755", dated Jun. 18, 2019, with English translation thereof, p. 1-p. 6.

Bruce D. Lucas; et al., "An Iterative Image Registration Technique with an Application to Stereo Vision," Proceedings of the 7th International Joint Conference on Artificial Intelligence (IJCAI '81), Aug. 24-28, 1981, pp. 674-679.

"Search Report of Europe Counterpart Application", dated Apr. 28, 2021, p. 1-p. 52.

* cited by examiner

FIG. 4

| 121 | 123 |
|---|---|
| MOTION PATTERN OF SCOPE HEAD | OPERATION INFORMATION |
| HORIZONTALLY SHAKING TWICE | SWITCHING LIGHT SOURCE |
| ROTATION IN OPTICAL AXIS DIRECTION OF SCOPE | CHANGING MAGNIFICATION |
| ⋮ | ⋮ |

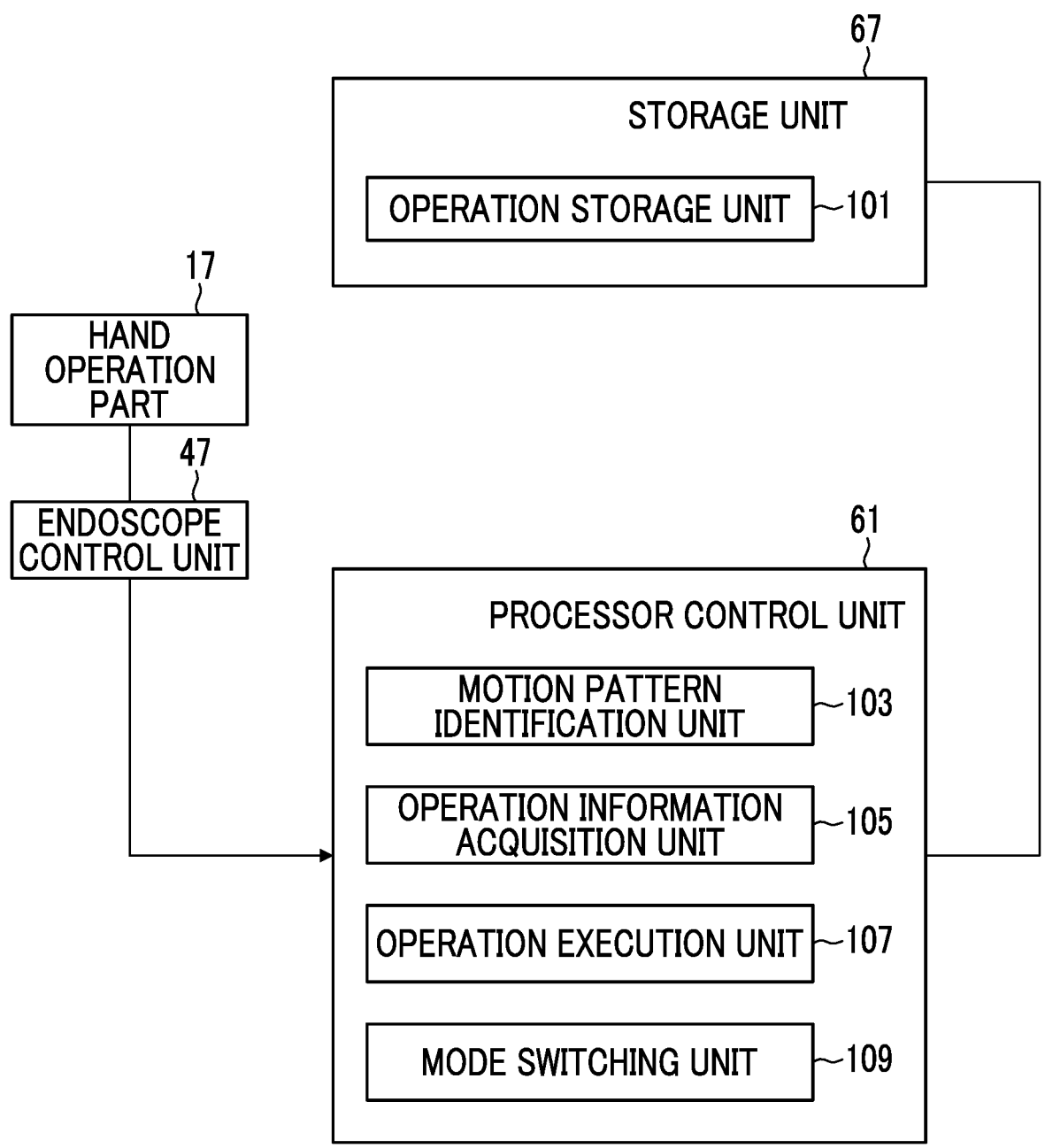

ENDOSCOPE DEVICE, ENDOSCOPE OPERATION METHOD, AND PROGRAM WITH MOTION PATTERN DETECTION

CROSS-REFERENCE TO RELATED APPLICATIONS

The present application is a Continuation of PCT International Application No. PCT/JP2019/014755 filed on Apr. 3, 2019 claiming priority under 35 U.S.C § 119(a) to Japanese Patent Application No. 2018-080800 filed on Apr. 19, 2018. Each of the above applications is hereby expressly incorporated by reference, in its entirety, into the present application.

BACKGROUND OF THE INVENTION

1. Field of the Invention

The present invention relates to an endoscope device, an endoscope operation method, and a program, and particularly to an information input method.

2. Description of the Related Art

In a case where an examination is performed using an endoscope device, an operator performs a diagnosis using an endoscopic image displayed on a display unit while performing a complicated scope operation using both hands. For example, the operator performs operations such as changing a magnification of an image, switching a light source, capturing a static image, air supply, suction, and water supply while observing the endoscopic image. Further, with the development of endoscope devices in the future, new operations of the endoscope devices may be added. Such operations are assigned to an input device such as a switch attached to an operation unit of a scope, but there is limitation on the number of input devices such as buttons and angle knobs attached to the operation unit of the scope. Accordingly, the number of operations which can be assigned to the existing input devices is limited.

In recent years, a technique for a diagnosis or assisting a diagnosis using artificial intelligence (AI) has been developed in the endoscope devices. It is necessary for the operator to perform an input for approval or disapproval of the AI diagnosis result. In this case, it is necessary for the operator to stop the examination, release his/her hand from the scope, and input information by clicking a mouse or the like. In this manner, inputting information after releasing his/her hand from the scope is a burden for the examination.

In the related art, various techniques for this problem have been proposed.

For example, JP2006-167139A has proposed a technique of enabling many operation functions to be used without increasing the number of buttons of an operation unit (of a scope) of an endoscope and without touching an operation panel of a processor of an endoscope device during an operation. Specifically, in the technique disclosed in JP2006-167139A, a normal operation mode and an extension operation mode are switched by detecting operations including half-pressing of two-stage push-down buttons, motions are assigned to the buttons of the operation unit for the respective operation modes.

SUMMARY OF THE INVENTION

However, in the technique disclosed in JP2006-167139A, different operations between the normal operation mode and the extension operation mode are assigned to one button in some cases, and thus the operator may confuse the assigned operations. In addition, in the technique disclosed in JP2006-167139A, since the switching of the operation mode is performed by detecting the operation of half-pressing of the two-stage push-down button, the two-stage push-down button has to be provided, and the operator has to perform a half-pressing operation.

The invention is made in view of such circumstances, and an object of the invention is to provide an endoscope device, an endoscope operation method, and a program which can allow the operator to simply perform operations using mechanisms and buttons of the operation unit already provided, without confusing the assigned operations.

An endoscope device as an aspect of the invention for achieving the object comprises a motion pattern identification unit that identifies a single or plurality of motion patterns indicating a specific movement of a scope head of a scope unit; an operation storage unit that stores a single or plurality of pieces of operation information for instructing an operation of the endoscope device, and the single or plurality of motion patterns of the scope head in association with each other; an operation information acquisition unit that acquires the operation information corresponding to the motion pattern from the operation storage unit on the basis of the motion pattern identified by the motion pattern identification unit; and an operation execution unit that executes an operation corresponding to the operation information acquired by the operation information acquisition unit.

According to the aspect, a motion pattern indicating a specific movement of the scope head is identified by the motion pattern identification unit, and an operation corresponding to the operation information of the motion pattern is executed by the operation execution unit. In the aspect, it is possible for the operator to simply perform operations using mechanisms and buttons of an operation unit already provided, without confusing the assigned operations.

It is preferable that the motion pattern identification unit identifies the motion pattern on the basis of time-series images acquired by an imaging unit included in the scope head.

According to the aspect, the motion pattern is identified by the motion pattern identification unit on the basis of the time-series images acquired by the imaging unit included in the scope head. In the aspect, it is possible to accurately identify the motion pattern without providing a sensor for identifying the motion pattern to the scope head.

It is preferable that the motion pattern identification unit calculates a movement vector in the time-series images, and identifies a motion pattern of the scope head on the basis of the movement vector.

According to the aspect, since the motion pattern identification unit calculates the movement vector in the time-series images and identifies the motion of the scope head on the basis of the movement vector, the motion pattern can be accurately identified.

It is preferable that the motion pattern identification unit identifies a motion pattern of the scope head on the basis of sensor information output from a sensor included in the scope unit.

According to the aspect, since the motion pattern of the scope head is identified by the motion pattern identification unit on the basis of the sensor information output from the sensor included in the scope unit, it is possible to reduce a processing load of identifying the motion pattern by image processing and to accurately identify the motion pattern.

It is preferable that the scope unit includes at least one of an acceleration sensor, a gyro sensor, a magnetic field sensor, a bend sensor, an infrared sensor, or an ultrasonic sensor.

It is preferable that the motion pattern identification unit identifies a motion pattern on the basis of input operation information that is input via an operation unit of the scope unit.

According to the aspect, since the motion pattern is identified by the motion pattern identification unit on the basis of the input operation information that is input via the operation unit of the scope unit, the movement of the scope head is identified directly from the operation of the operation unit by the operator.

It is preferable that the endoscope device further comprises a mode switching unit that switches between a scope head motion input mode in which the operation execution unit executes the operation, and a normal observation mode in which the operation execution unit does not execute the operation.

According to the aspect, the scope head motion input mode and the normal observation mode are switched by the mode switching unit. In the aspect, it is possible to perform normal observation by moving the scope head, and to input a predetermined operation by moving the scope head.

It is preferable that the operation storage unit stores the operation information for instructing a mode switching operation in the mode switching unit, and the single or plurality of motion patterns of the scope head in association with each other.

According to the aspect, the operation information for instructing the mode switching operation in the mode switching unit and the single or plurality of motion patterns of the scope head are stored in the operation storage unit in association with each other. In the aspect, the mode switching is performed by the motion of the scope head, and thus it is possible to more simply perform an operation.

It is preferable that the operation storage unit stores the operation information regarding an adjustment operation for observation conditions and the single or plurality of motion patterns in association with each other.

According to the aspect, the operation information regarding the adjustment operation for observation conditions and the single or plurality of motion patterns are stored in the operation storage unit in association with each other. In the aspect, it is possible to perform an operation regarding the adjustment operation for observation conditions by the motion of the scope head.

It is preferable that the operation storage unit stores an input operation for approval or disapproval and the single or plurality of motion patterns of the scope head in association with each other.

According to the aspect, the input operation for approval or disapproval and the single or plurality of motion patterns of the scope head are stored in the operation storage unit in association with each other. In the aspect, the input for approval or disapproval can be performed by the motion of the scope head.

It is preferable that the operation storage unit stores a bending motion of the scope head in a vertical direction in association with the input operation for approval, and stores a bending motion of the scope head in a horizontal direction in association with the input operation for disapproval.

According to the aspect, the bending motion of the scope head in the vertical direction is stored in the operation storage unit in association with the input operation for approval, and the bending motion of the scope head in the horizontal direction is stored in the operation storage unit in association with the input operation for disapproval. In the aspect, it is possible to perform intuitive operations by causing the scope head to perform a nod motion of a person as the input for approval, causing the scope head to perform a motion of a person shaking his/her neck as the input for disapproval.

It is preferable that the motion pattern includes at least one piece of information on the number of times or speed of the specific movement of the scope head.

An endoscope operation method as another aspect of the invention includes identifying a single or plurality of motion patterns indicating a specific movement of a scope head of a scope unit; acquiring, from an operation storage unit, which stores a single or plurality of pieces of operation information for instructing an operation of an endoscope device and the single or plurality of motion patterns of the scope head in association with each other, the operation information corresponding to the motion pattern on the basis of the motion pattern identified in the identifying of the motion pattern; and executing an operation corresponding to the operation information.

A program as still another aspect of the invention causes a computer to execute an endoscope operation method including identifying a single or plurality of motion patterns indicating a specific movement of a scope head of a scope unit; acquiring, from an operation storage unit, which stores a single or plurality of pieces of operation information for instructing an operation of an endoscope device and the single or plurality of motion patterns of the scope head in association with each other, the operation information corresponding to the motion pattern on the basis of the motion pattern identified in the identifying of the motion pattern; and executing an operation corresponding to the operation information.

According to the invention, since the motion pattern indicating the specific movement of the scope head is identified by the motion pattern identification unit and the operation corresponding to the operation information of the motion pattern is executed by the operation execution unit, it is possible for the operator to simply perform operations using mechanisms and buttons of the operation unit already provided, without confusing the assigned operations.

BRIEF DESCRIPTION OF THE DRAWINGS

FIG. 4 is a diagram illustrating a storage configuration example of an operation storage unit.

FIG. 14 is a block diagram illustrating a functional configuration example.

DESCRIPTION OF THE PREFERRED EMBODIMENTS

Hereinafter, preferred embodiments of an endoscope device, an endoscope operation method, and a program according to the invention will be described with reference to the accompanying drawings.

Figure 1:
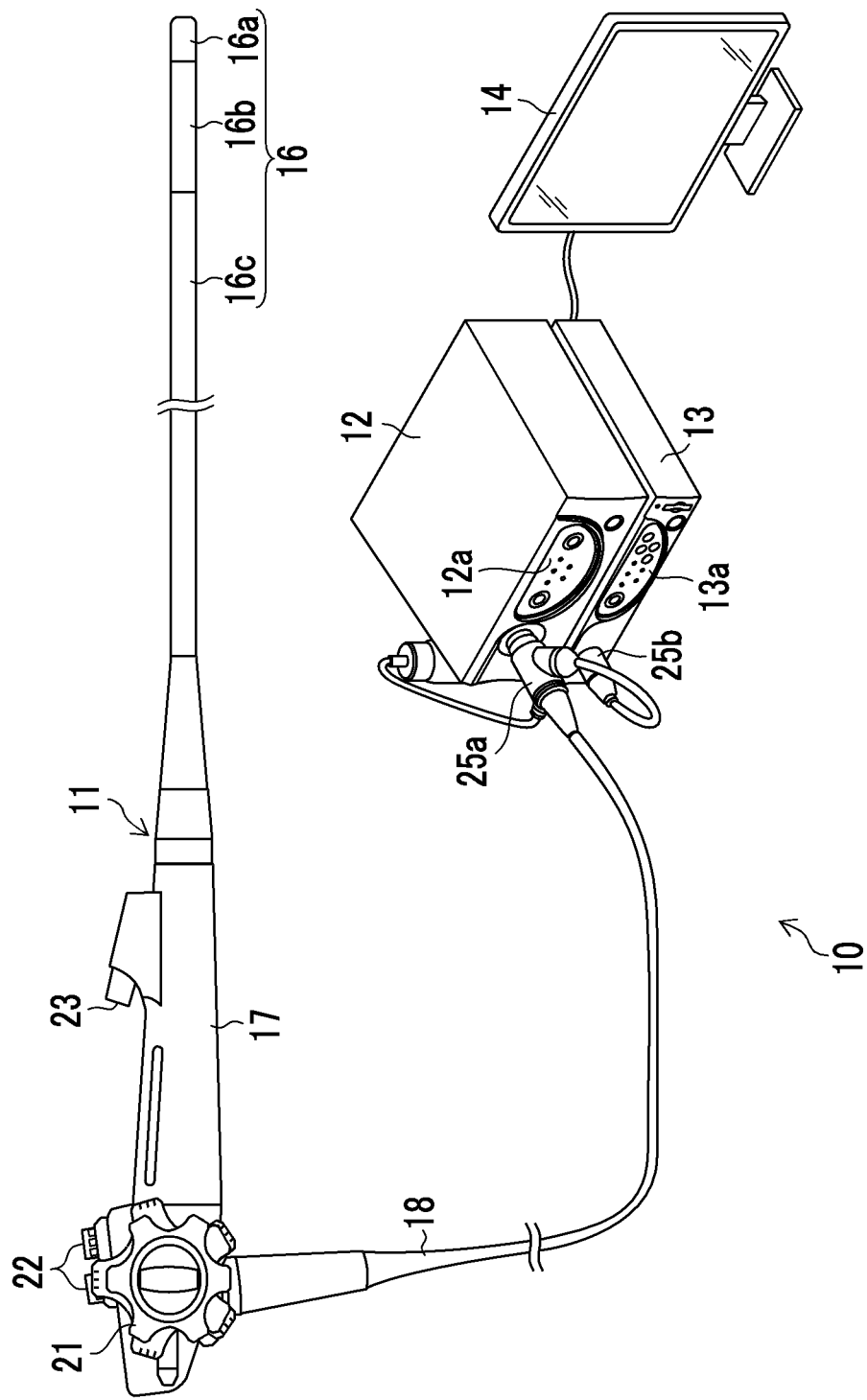
FIG. 1 is an external perspective view of an endoscope device.

FIG. 1 is an external perspective view of an endoscope device 10.

The endoscope device 10 illustrated in FIG. 1 comprises roughly an endoscope scope (here, flexible endoscope) (scope unit) 11 that images an observation target in a subject, a light source device 12, a processor device 13, and a display 14 such as a liquid crystal monitor.

The light source device 12 supplies various kinds of illumination light such as white light for capturing a normal image and light in a specific wavelength range for capturing a special light image to the endoscope scope 11.

The processor device 13 can also function as one form of the endoscope device 10, and has a function of generating image data of a normal image and/or a special light image for display or recording on the basis of image signals obtained by the endoscope scope 11.

The display 14 displays a normal image or a special light image on the basis of the image data for display which is input from the processor device 13.

The endoscope scope 11 comprises a flexible insertion part 16 to be inserted into the subject, a hand operation part (operation unit of a scope unit) 17 which is provided to be continuous to a proximal end portion of the insertion part 16 and is used for gripping the endoscope scope 11 and operating the insertion part 16, and a universal cord 18 that connects the hand operation part 17 to the light source device 12 and the processor device 13.

Figure 2:
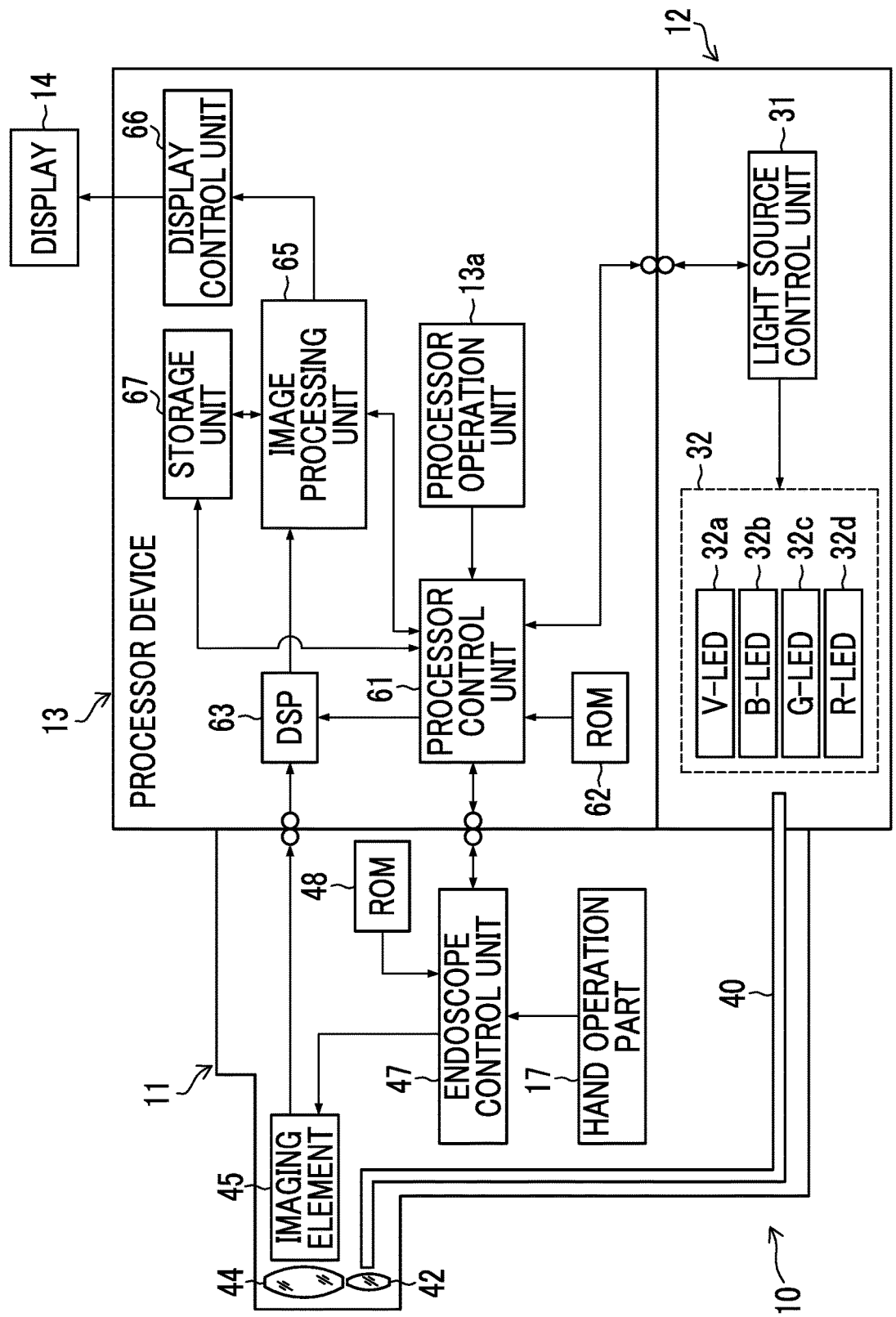
FIG. 2 is a block diagram illustrating an electric configuration of the endoscope device.

An illumination lens 42, an objective lens 44, an imaging element (imaging unit) 45, and the like are built in an insertion part-distal end portion 16a which is a distal end portion of the insertion part 16 (refer to FIG. 2). A bendable portion 16b which is bendable is provided to be continuous to a rear end of the insertion part-distal end portion 16a. In addition, a flexible tube portion 16c having flexibility is provided to be continuous to a rear end of the bendable portion 16b. The insertion part-distal end portion 16a and the bendable portion 16b constitute a scope head.

The hand operation part 17 is provided with an angle knob 21, an operation button 22, a forceps inlet 23, and the like. The angle knob 21 is rotated in a case of adjusting a bending direction and a bending amount of the bendable portion 16b. The operation button 22 is used for various kinds of operations such as air supply, water supply, and suction. The forceps inlet 23 communicates with a forceps channel in the insertion part 16. An up-down angle knob that moves the bendable portion 16b up and down and a left-right angle knob that moves the bendable portion 16b left and right are provided to the angle knob 21.

An air supply and/or water supply channel, a signal cable, a light guide 40, and the like are incorporated in the universal cord 18. A connector part 25a connected to the light source device 12 and a connector part 25b connected to the processor device 13 are provided to a distal end portion of the universal cord 18. As a result, illumination light is supplied from the light source device 12 to the endoscope scope 11 via the connector part 25a, and image signals obtained by the endoscope scope 11 are input to the processor device 13 via the connector part 25b.

In addition, a light source operation unit 12a such as a power button, a lighting button to turn on a light source, and a brightness adjustment button is provided to the light source device 12, and a processor operation unit 13a including a power button and an input unit (not illustrated) that accepts an input from a pointing device such as a mouse is provided to the processor device 13.

First Embodiment

FIG. 2 is a block diagram illustrating an electric configuration of the endoscope device 10.

As illustrated in FIG. 2, the endoscope scope 11 has roughly the light guide 40, the illumination lens 42, the objective lens 44, the imaging element 45, the hand operation part 17, an endoscope control unit 47, and a read only memory (ROM) 48.

A large diameter optical fiber, a bundle fiber, or the like is used as the light guide 40. An incident end of the light guide 40 is inserted into the light source device 12 via the connector part 25a, and an emission end of the light guide 40 faces the illumination lens 42 provided in the insertion part-distal end portion 16a through the insertion part 16. The illumination light supplied from the light source device 12 to the light guide 40 is emitted to the observation target through the illumination lens 42. Then, the illumination light reflected and/or scattered by the observation target is incident on the objective lens 44.

The objective lens 44 forms the incident reflected light or scattered light (that is, an optical image of the observation target) of the illumination light on an imaging surface of the imaging element 45.

The imaging element 45 is a complementary metal oxide semiconductor (CMOS) type or charge coupled device (CCD) imaging element, and is positioned and fixed relative to the objective lens 44 at a position on the inner side of the objective lens 44. A plurality of pixels configured by a plurality of photoelectric conversion elements (photodiodes) that photoelectrically convert the optical image are two-dimensionally arranged on the imaging surface of the imaging element 45. In addition, on the incident surface side of the plurality of pixels of the imaging element 45 in this example, red (R), green (G), and blue (B) color filters are arranged for each pixel, and thus R pixels, G pixels, and B pixels are formed. The filter array of the RGB color filters is generally a Bayer array, but is not limited thereto.

The imaging element 45 converts the optical image formed by the objective lens 44 into an electrical image signal, and outputs the electrical image signal to the processor device 13.

In a case where the imaging element 45 is a CMOS type, an analog/digital (A/D) converter is built in the imaging element 45, and a digital image signal is directly output from the imaging element 45 to the processor device 13. Further, in a case where the imaging element 45 is a CCD type, the image signal output from the imaging element 45 is converted into a digital image signal by an A/D converter (not illustrated) or the like, and then is output to the processor device 13.

The hand operation part 17 has an imaging mode setting unit for setting a static image capturing button (not illustrated), a normal image capturing mode, and a special light image capturing mode.

The endoscope control unit 47 sequentially executes various kinds of program or data read from the ROM 48 or the like according to the operation on the hand operation part 17, and mainly controls driving of the imaging element 45. For example, in a case of the normal image capturing mode, the endoscope control unit 47 controls the imaging element 45 to read signals of the R pixels, G pixels, and B pixels of the imaging element 45. Further, in the special light image capturing mode, in a case where violet light is emitted from a V-LED 32a or in a case where blue light is emitted from a B-LED 32b as the illumination light for acquiring a special light image, the endoscope control unit 47 controls the imaging element 45 to read only the signals of the B pixels of the imaging element 45 which have spectral sensitivity in a wavelength range of the violet light and the blue light.

The endoscope control unit 47 performs communication with a processor control unit 61 of the processor device 13, and transmits input operation information from the hand operation part 17, identification information for identifying the kinds of endoscope scope 11 stored in the ROM 48, and the like to the processor device 13.

The light source device 12 has a light source control unit 31 and a light source unit 32. The light source control unit 31 controls the light source unit 32, and performs communication with the processor control unit 61 of the processor device 13 to exchange various kinds of information.

The light source unit 32 has a plurality of semiconductor light sources, for example. In the embodiment, the light source unit 32 has LEDs of four colors, the violet light emitting diode (V-LED) 32a, the blue light emitting diode (B-LED) 32b, a green light emitting diode (G-LED) 32c, and a red light emitting diode (R-LED) 32d. The V-LED 32a is a violet semiconductor light source that emits violet light in a wavelength range of 380 to 420 nm with a center wavelength of 405 nm. The B-LED 32b is a blue semiconductor light source that emits blue light in a wavelength range of 420 to 500 nm with a center wavelength of 460 nm. The G-LED 32c is a green semiconductor light source that emits green light in a wavelength range of 480 to 600 nm. The R-LED 32d is a red semiconductor light source that emits red light in a wavelength range of 600 to 650 nm with a center wavelength of 620 to 630 nm. The center wavelength of each of the V-LED 32a and the B-LED 32b has a width of about ±5 nm to ±10 nm.

Turning on or off each of the LEDs 32a to 32d, a light emission amount at the time of lighting thereof, and the like can be controlled by inputting an independent control signal to each of the LEDs 32a to 32d by the light source control unit 31. In the normal image capturing mode, the light source control unit 31 turns on all of the V-LED 32a, the B-LED 32b, the G-LED 32c, and the R-LED 32d. Therefore, in the normal image capturing mode, white light including violet light, blue light, green light, and red light is used as the illumination light.

On the other hand, in a special light image capturing mode, in a case where the light source control unit 31 turns on at least one light source or a plurality of appropriately combined light sources among the V-LED 32a, the B-LED 32b, the G-LED 32c, and the R-LED 32d or turns on a plurality of light sources, the light emission amount (light intensity ratio) of each light source is controlled, and thereby images of a plurality of layers with different depths of the subject can be captured.

The light of the respective colors emitted from the LEDs 32a to 32d is incident on the light guide 40 inserted into the endoscope scope 11 via an optical path coupling portion formed of a mirror, a lens, and the like, and a stop mechanism (not illustrated).

As the illumination light of the light source device 12, light in various wavelength ranges is selected according to the observation purpose, such as white light (light in white-light wavelength range or light in a plurality of wavelength ranges) or light (special light) in one or a plurality of specific wavelength ranges, or a combination thereof. The specific wavelength range of the special light is a range narrower than the white-light wavelength range.

A first example of the specific wavelength range is a blue-light wavelength range or a green-light wavelength range of a visible-light wavelength range, for example. The wavelength range of the first example includes a wavelength range of 390 nm to 450 nm or 530 nm to 550 nm, and light of the first example has a peak wavelength in a wavelength range of 390 nm to 450 nm or 530 nm to 550 nm.

A second example of the specific wavelength range is a red-light wavelength range of a visible-light wavelength range, for example. The wavelength range of the second example includes a wavelength range of 585 nm to 615 nm or 610 nm to 730 nm, and light of the second example has a peak wavelength in a wavelength range of 585 nm to 615 nm or 610 nm to 730 nm.

A third example of the specific wavelength range includes a wavelength range where a light absorption coefficient in oxyhemoglobin is different from that in reduced hemoglobin, and light of the third example has a peak wavelength in a wavelength range where a light absorption coefficient in oxyhemoglobin is different from that in reduced hemoglobin. The wavelength range of the third example includes a wavelength range of 400±10 nm, 440±10 nm, 470±10 nm, or 600 nm to 750 nm, and light of the third example has a peak wavelength in a wavelength range of 400±10 nm, 440±10 nm, 470±10 nm, or 600 nm to 750 nm.

A fourth example of the specific wavelength range is a wavelength range (390 nm to 470 nm) of excitation light which is used for observation (fluorescence observation) of fluorescence emitted by fluorescent materials in a living body and excites the fluorescent materials.

A fifth example of the specific wavelength range is an infrared wavelength range. The wavelength range of the fifth example includes a wavelength range of 790 nm to 820 nm or 905 nm to 970 nm, and light of the fifth example has a peak wavelength in a wavelength range of 790 nm to 820 nm or 905 nm to 970 nm.

The processor device 13 has the processor operation unit 13a, the processor control unit 61, a ROM 62, a digital signal processor (DSP) 63, an image processing unit 65, a display control unit 66, a storage unit 67, and the like.

The processor operation unit 13a includes the power button, the input unit that accepts an input such as coordinate position and click (execution instruction) instructed on the display 14 by the mouse, and the like.

The processor control unit 61 sequentially performs processing by reading necessary programs or data from the ROM 62 according to the input operation information on the processor operation unit 13a and the input operation information on the hand operation part 17 which is received via the endoscope control unit 47 to control each unit of the processor device 13, and controls the light source device 12. The processor control unit 61 may accept a necessary instruction input from other external devices such as a keyboard connected via an interface (not illustrated).

The DSP 63 which functions as a form of an image acquisition unit that acquires image data of each frame of a video output from the endoscope scope 11 (imaging element 45) performs various kinds of signal processing such as defect correction processing, offset processing, white balance correction, gamma correction, and demosaicing processing on the image data for one frame of the video input from the endoscope scope 11 to generate image data for one frame under the control of the processor control unit 61.

The image processing unit 65 receives an input of the image data from the DSP 63, performs image processing such as color conversion processing, color emphasis processing, and structure emphasis processing as necessary on the input image data, and generates image data indicating an endoscopic image in which the observation target is shown. The color conversion processing is processing for performing color conversion by 3×3 matrix processing, gradation conversion processing, three-dimensional lookup table processing, and the like on the image data. The color emphasis processing is processing for emphasizing color in a direction making difference in tint between, for example, blood vessels and mucous membranes on the image data that has been subjected to the color conversion processing. The structure emphasis processing is processing for emphasizing specific tissues or structures included in the observation target, such as blood vessels or pit patterns, and is performed on the image data that has been subjected to the color emphasis processing.

In a case where there is an imaging instruction for a static image or video, the image data of each frame of the video processed by the image processing unit 65 is recorded in the storage unit 67 as the static image or video instructed to be captured.

The display control unit 66 generates display data for displaying the normal image and the special light image on the display 14 from the input image data, outputs the generated display data to the display 14, and displays a display image on the display 14.

Figure 3:
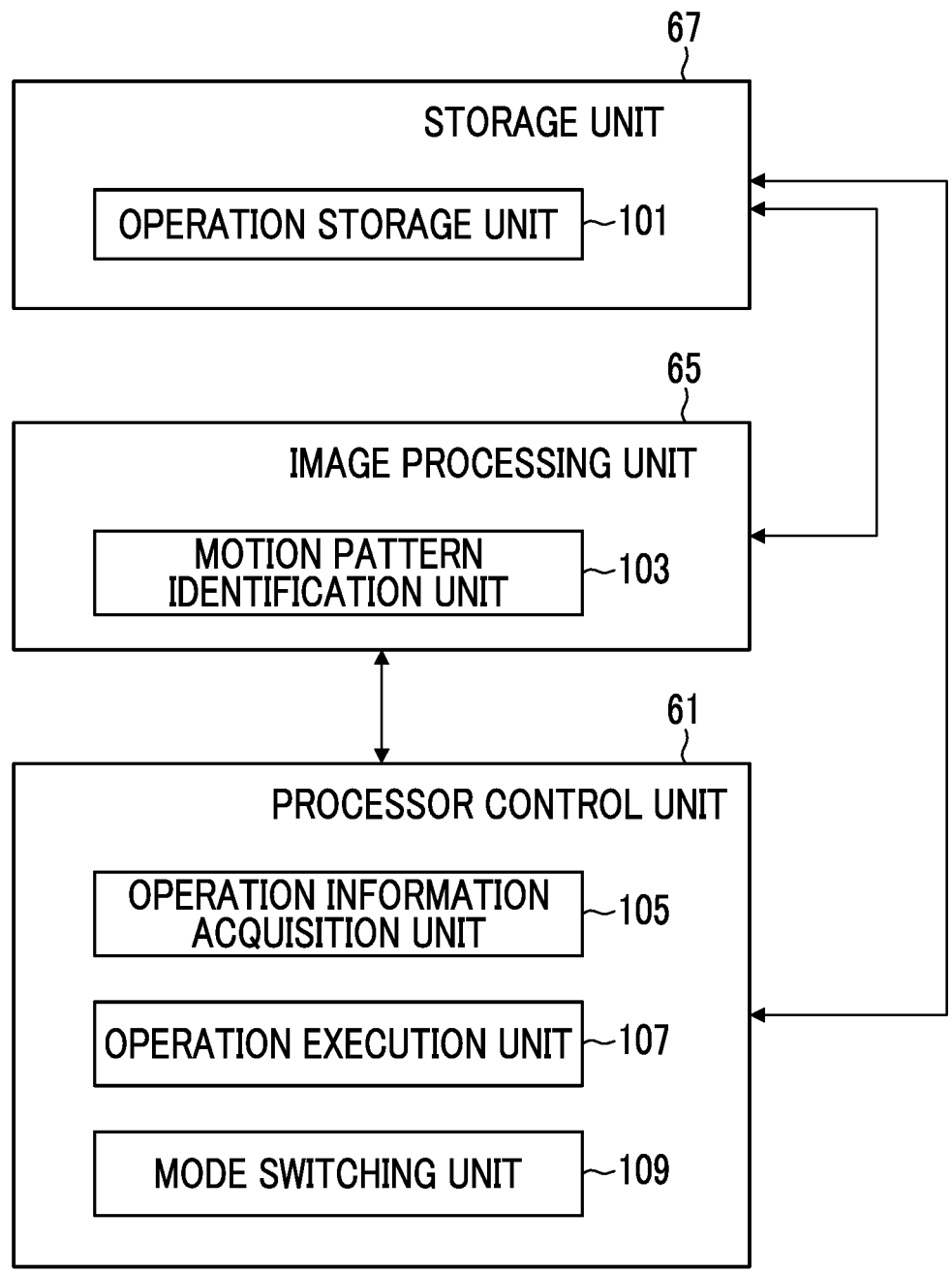
FIG. 3 is a block diagram illustrating a functional configuration example.

FIG. 3 is a block diagram illustrating a main functional configuration example of the embodiment.

In the embodiment, an operation storage unit 101 is provided to the storage unit 67, a motion pattern identification unit 103 is provided to the image processing unit 65, and an operation information acquisition unit 105, an operation execution unit 107, and a mode switching unit 109 are provided to the processor control unit 61.

The operation storage unit 101 stores motion patterns of the scope head (the insertion part-distal end portion 16a and the bendable portion 16b) and operation information for instructing an operation of the endoscope device 10 in association with each other. Here, the motion patterns are patterns indicating specific movements of the scope head, and the motion patterns are configured by movements of a single or plurality of scope heads. In addition, the operation information is information indicating a motion command to the processor device 13, the light source device 12, and the endoscope scope 11.

FIG. 4 is a diagram illustrating a storage configuration example of the operation storage unit 101.

As illustrated in FIG. 4, a motion pattern 121 of the scope head and operation information 123 are stored in association with each other in the operation storage unit 101. The motion pattern 121 of the scope head and the operation information 123 regarding an adjustment operation for observation conditions of the scope unit are stored in association with each other. "Horizontally shaking twice" as the motion pattern 121 of the scope head is stored in association with "switching a light source" as the operation information 123. In addition, "rotation in an optical axis direction of the scope" as the motion pattern 121 of the scope head is stored in association with "changing a magnification" as the operation information 123. In a case of changing a parameter which takes continuous values such as a magnification, a rotation angle may be notified to the motion pattern identification unit 103, and the parameter which takes continuous values may be changed according to the rotation angle.

In addition, in the operation storage unit 101, operation information for instructing a mode switching operation of the mode switching unit 109, which will be described below, and the motion pattern of the scope head may be stored in association with each other.

The motion pattern identification unit 103 identifies a motion pattern indicating a specific movement of the scope head. The motion pattern identification unit 103 of the embodiment detects the movement of the scope head on the basis of time-series images acquired by the imaging element 45 included in the scope head to identify the motion pattern. Specifically, the motion pattern identification unit 103 calculates a movement vector in the time-series images, and detects the movement of the scope head on the basis of the calculated movement vector. Then, the motion pattern identification unit 103 compares the detected movement of the scope head with the motion pattern of the scope head stored in the operation storage unit 101, and determines whether the detected movement of the scope head matches the motion pattern of the scope head stored in the operation storage unit 101. The identification of the motion pattern by the image processing will be described below in detail.

The operation information acquisition unit 105 acquires the operation information corresponding to the motion pattern from the operation storage unit 101 on the basis of the motion pattern identified by the motion pattern identification unit 103. Specifically, the operation information acquisition unit 105 acquires the motion pattern of the scope head identified by the motion pattern identification unit 103, and acquires the operation information associated with the motion pattern stored in the operation storage unit 101 which corresponds to the motion pattern.

The operation execution unit 107 executes the operation corresponding to the operation information acquired by the operation information acquisition unit 105. Specifically, the operation execution unit 107 operates the processor device 13, the light source device 12, and/or the endoscope scope 11 according to the operation information.

The mode switching unit 109 switches between a scope head motion input mode in which the operation execution unit 107 executes the operation and a normal observation mode in which the operation execution unit 107 does not execute the operation. The normal observation mode and the scope head motion input mode are set in the endoscope device 10, and the mode switching between the normal observation mode and the scope head motion input mode is performed by the mode switching unit 109. In the scope head motion input mode, in a case where the operator performs a specific motion of the scope head, an operation registered by being assigned to the motion is performed. On the other hand, in the normal observation mode, even in a case where the operator performs a specific motion of the scope head, normal observation is performed without performing the assigned operation. However, in a case of an example of a command for mode switching to be described below, even in the normal observation mode, an operation (mode switching) is executed by the specific movement of the scope head.

As an input of a command for mode switching to the mode switching unit 109, for example, a command is input by a mode switching button (not illustrated) provided to the hand operation part 17. Specifically, the normal observation mode and the scope head motion input mode are switched each time the mode switching button is pressed. In addition, for example, the mode is switched to the scope head motion input mode while the mode switching button is pressed, and the mode is switched to the normal observation mode in a case of releasing the mode switching button.

As another example of an input of a command for mode switching to the mode switching unit 109, an input by the movement of the scope head can be considered. In this case, the motion pattern for mode switching is made not to overlap the other motion patterns. For example, in a case where "horizontally shaking" is set as the motion pattern associated with operation information other than the mode switching, "vertically shaking" is set as the motion pattern associated with the operation information for the mode switching. In addition, in a case where "horizontally shaking twice" is set as the motion pattern associated with operation information other than the mode switching, "horizontally shaking five times quickly" is set as the motion pattern associated with the operation information for the mode switching so that the motion pattern for the mode switching is made not to overlap the other motion patterns.

Figure 5:
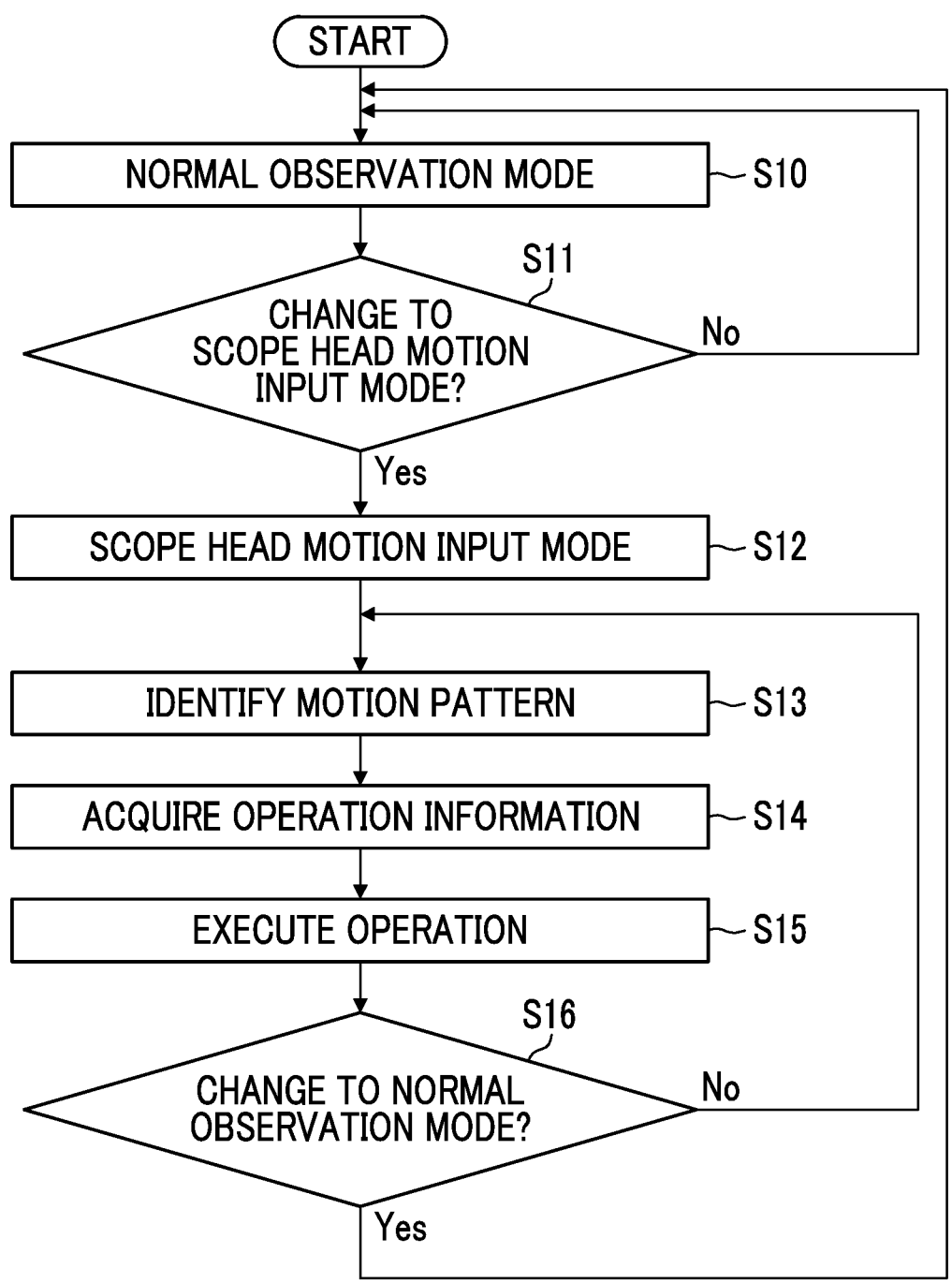
FIG. 5 is a flowchart illustrating an operation method of an endoscope.

FIG. 5 is a flowchart illustrating an operation method of an endoscope using the endoscope device 10.

First, observation is performed by the endoscope device 10 in the normal observation mode (Step S10). Then, it is determined whether the normal observation mode is changed to the scope head motion input mode by the mode switching unit 109 (Step S11). In a case where the mode switching is not performed, the normal observation mode is continued.

On the other hand, in a case where the mode switching is performed, the normal observation mode is changed to the scope head motion input mode by the mode switching unit 109 (Step S12).

Then, the motion pattern of the scope head is identified by the motion pattern identification unit 103 (Step S13). The operation information associated with the motion pattern identified by the motion pattern identification unit 103 is acquired by the operation information acquisition unit 105 (Step S14). Then, the operation is executed by the operation execution unit 107 (Step S15).

Then, it is determined whether the scope head motion input mode is changed to the normal observation mode by the mode switching unit 109 (Step S16). Here, the change to the normal observation mode is performed in a case where a certain time has passed after switching to the scope head motion input mode or in a case where the motion pattern is identified by the motion pattern identification unit 103 a certain number of times or more, for example. In a case where the mode switching is not performed, the scope head motion input mode is continued.

On the other hand, in a case where the mode switching is performed, the scope head motion input mode is changed to the normal observation mode by the mode switching unit 109 (Step S10).

As described above, according to the embodiment, the motion pattern indicating the specific movement of the scope head is identified, and the operation corresponding to the operation information of the motion pattern is executed. As a result, without increasing special mechanisms and the number of buttons of the operation unit, it is possible for the operator to simply perform operations without confusing the assigned operations.

In the embodiment, the hardware structures of processing units executing various kinds of processing are the following various processors. The various processors include a central processing unit (CPU) as a general-purpose processor executing software (program) and functioning as various processing units, a programmable logic device (PLD) as a processor of which the circuit configuration can be changed after manufacturing such as a field programmable gate array (FPGA), and a dedicated electrical circuit as a processor having a circuit configuration designed exclusively for executing a specific process such as an application specific integrated circuit (ASIC).

One processing unit may be configured by one processor among these various processors, or may be configured by two or more same or different kinds of processors (for example, a combination of a plurality of FPGAs or a combination of the CPU and the FPGA). In addition, a plurality of processing units may be configured by one processor. As an example where a plurality of processing units are configured by one processor, first, there is a form in which one processor is configured by a combination of one or more CPUs and software as typified by a computer, such as a client or a server, and this processor functions as a plurality of processing units. Second, there is a form in which a processor fulfilling the functions of the entire system including a plurality of processing units by one integrated circuit (IC) chip as typified by a system on chip (SoC) or the like is used. In this manner, various processing units are configured by using one or more of the above-described various processors as hardware structures.

Furthermore, the hardware structures of these various processors are more specifically electrical circuitry where circuit elements, such as semiconductor elements, are combined.

The above-described configurations and functions can be appropriately realized by any hardware or software, or a combination of hardware and software. For example, the invention can be applied to a program causing a computer to execute the above-described processing steps (processing procedure), a computer-readable recording medium (non-temporary recording medium) in which such a program is recorded, or a computer in which such a program can be installed.

EXAMPLE

Next, specific movements of the scope head and inputs for the operation will be described.

As an example of the operation information stored in the operation storage unit 101, there is an input operation for approval or disapproval. In the following example, an example of performing an input operation for approval or disapproval by the movement of the scope head will be described.

Figure 6:
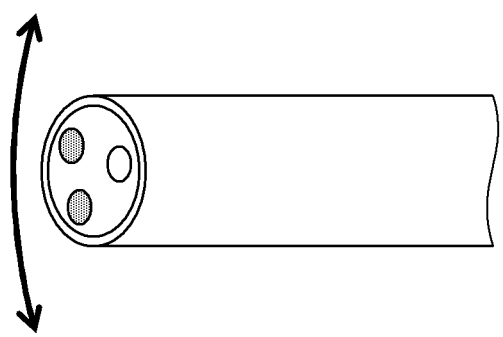
FIG. 6 is a diagram regarding a movement of a scope head.
Figure 7:
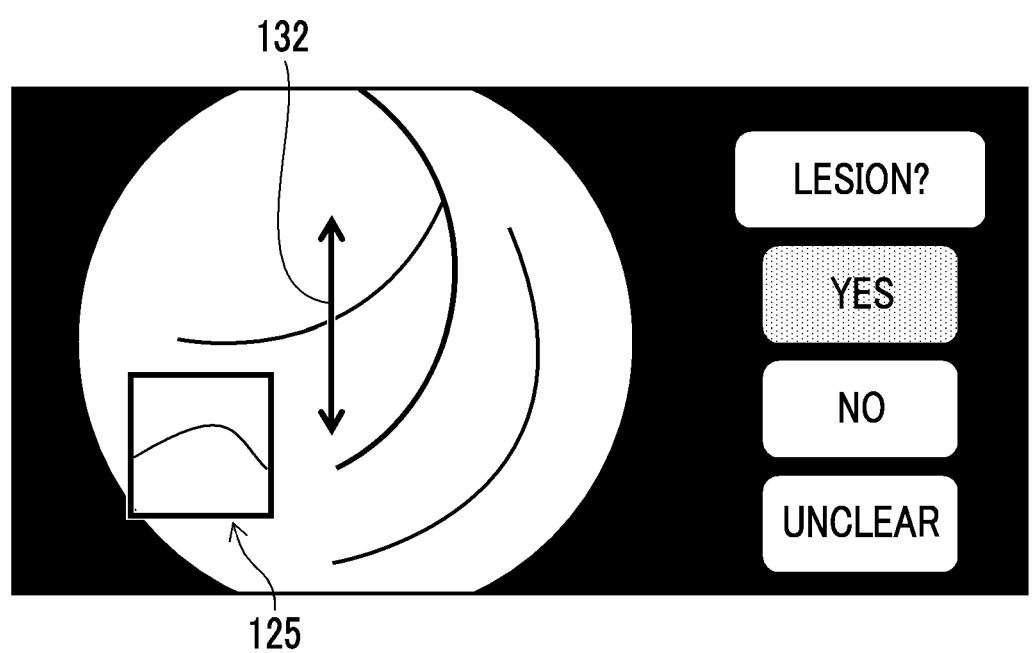
FIG. 7 illustrates a lesion detection result.
Figure 8:
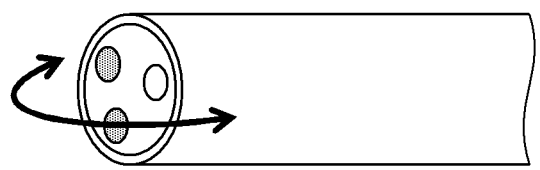
FIG. 8 is a diagram regarding a movement of the scope head.
Figure 9:
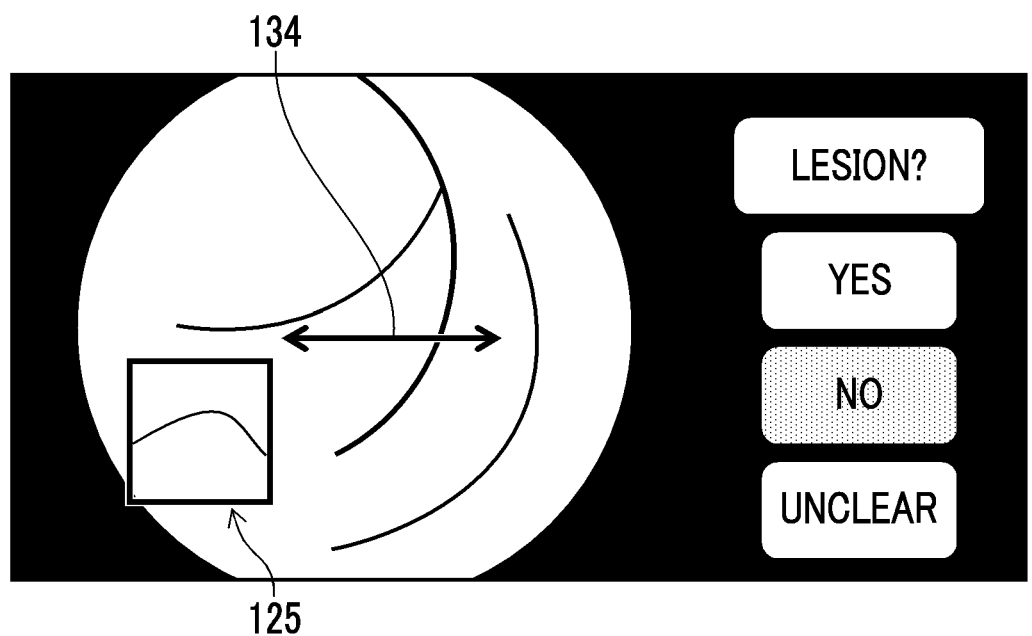
FIG. 9 illustrates a lesion detection result.
Figure 10:
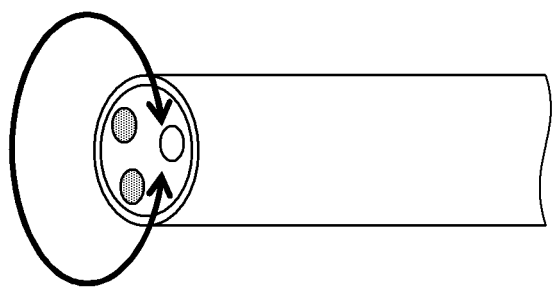
FIG. 10 is a diagram regarding a movement of the scope head.
Figure 11:
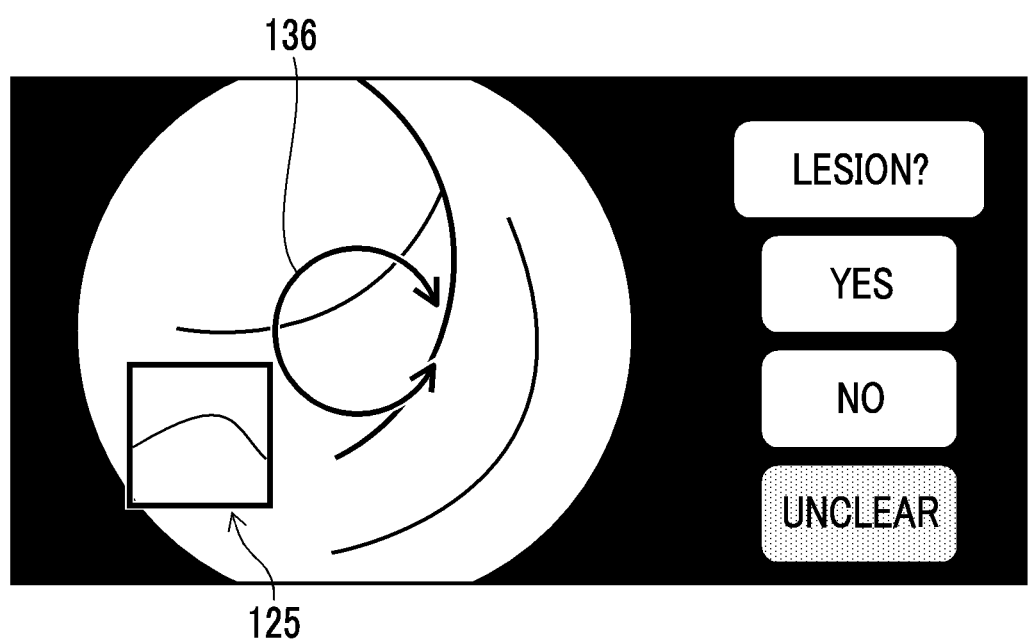
FIG. 11 illustrates a lesion detection result.

FIGS. 6 to 11 are explanatory diagrams of the endoscope system that performs a diagnosis based on the image captured during the endoscope examination, using AI in real time. The AI mounted in the endoscope system detects a lesion area from the endoscopic image. FIGS. 6, 8, and 10 are diagrams regarding the movements of the scope head, and FIGS. 7, 9, and 11 illustrate the lesion detection results of the AI displayed on the display 14. The operator checks a lesion detection result 125 of the AI displayed on the display 14, and performs an input for approval, disapproval, or unclearness by using the specific movement of the scope head.

FIGS. 6 and 7 illustrate a case of performing an input operation for approval regarding the lesion detection result 125. As illustrated in FIG. 6, a scope head performs a bending motion in a vertical direction, and the bending motion is identified as the motion pattern by the motion pattern identification unit 103. Here, the bending motion in the vertical direction means that the bendable portion 16*b* is bent by using the up-down angle knob to perform the motion. FIG. 7 illustrates a movement vector 132 corresponding to the bending motion of the scope head in a vertical direction illustrated in FIG. 6. The motion pattern identification unit 103 analyzes the movement vector 132, and identifies the motion pattern of the scope head. The bending motion of the scope head in the vertical direction is identified by the motion pattern identification unit 103, and on the basis of approval operation information corresponding to the bending motion, an input for approval is performed by the operation execution unit 107 (in FIG. 7, "Yes" is selected).

FIGS. 8 and 9 illustrate a case of performing an input operation for disapproval regarding the lesion detection result 125. As illustrated in FIG. 8, the scope head performs a bending motion in the horizontal direction, and the bending motion is identified as the motion pattern by the motion pattern identification unit 103. Here, the bending motion in the horizontal direction means that the bendable portion 16*b* is bent by using the left-right angle knob to perform the motion. FIG. 9 illustrates a movement vector 134 corresponding to the bending motion of the scope head in the horizontal direction illustrated in FIG. 8. The motion pattern identification unit 103 analyzes the movement vector 134, and identifies the motion pattern of the scope head. The bending motion of the scope head in the horizontal direction is identified by the motion pattern identification unit 103, and on the basis of disapproval operation information corresponding to the bending motion, an input for disapproval is performed by the operation execution unit 107 (in FIG. 9, "No" is selected).

FIGS. 10 and 11 illustrate a case of performing an input operation for unclarity regarding the lesion detection result 125. As illustrated in FIG. 10, the scope head performs a rotating motion in the optical axis direction, and the rotating motion is identified as the motion pattern by the motion pattern identification unit 103. Here, the rotating motion means that the hand operation part 17 is rotated to perform the motion. FIG. 11 illustrates a movement vector 136 corresponding to the rotating motion of the scope head illustrated in FIG. 10. The motion pattern identification unit 103 analyzes the movement vector 136, and identifies the motion pattern of the scope head. The rotating motion of the scope head is identified by the motion pattern identification unit 103, and on the basis of unclearness operation information corresponding to the rotating motion, an input for unclearness is performed by the operation execution unit 107 (in FIG. 9, "Unclear" is selected).

As described above, in a case of an input for approval, the input is performed by the bending motion in the vertical direction. This motion imitates a nod motion of a person, and the input can be performed by an intuitive motion for approval. Further, in a case of an input for disapproval, the input is performed by the bending motion in the horizontal direction. This motion imitates a motion of a person shaking his/her neck sideways, and the input can be performed by an intuitive motion for disapproval. Further, in a case of an input for unclearness, the input is performed by the rotating motion in the optical axis direction. This motion imitates a motion of a person tilting his/her neck, and the input can be performed by an intuitive motion for unclearness.

<Identification of Motion Pattern by Image Processing>

Next, the identification of the motion pattern by the image processing performed by the motion pattern identification unit 103 will be described. The motion pattern identification unit 103 analyzes the time-series images during the endoscope examination, and identifies the motion pattern. For example, examples of the motion pattern include (1) "vertically shaking", (2) "horizontally shaking", (3) "rotating", and (4) "moving forward and backward" the scope head.

In a case where the frame number of the endoscopic image at a certain time is t, the motion pattern identification unit 103 compares at least one or more images of frames before t-1-th frame with the image of the t-th frame, and identifies a case where the direction of the movement vector of the pixels is the vertical direction as the motion pattern of (1), a case where the direction of the movement vector of the pixels is the horizontal direction as the motion pattern of (2), a case where the direction of the movement vector of the pixels is a vector drawing a circle around the center of the image as the motion pattern of (3), and a case where the direction of the movement vector of the pixels is a vector moving toward the center or moving away from the center as the motion pattern of (4).

Since the method that the motion pattern identification unit 103 calculates the movement vector in the time-series images is a known technique, a detailed description is omitted here. For example, as the method of calculating the movement vector of pixel from the time-series images, an algorithm for extracting and tracking feature points such as corners and edges from images can be considered. As a representative algorithm, a KLT tracker (Bruce D. Lucas and Takeo Kanade. An Iterative Image Registration Technique with an Application to Stereo Vision. International Joint Conference on Artificial Intelligence, pages 674-679, 1981) and the like are exemplified.

Second Embodiment

Next, a second embodiment will be described. The motion pattern identification unit 103 of the embodiment identifies a motion pattern on the basis of sensor information output from a sensor 70.

Figure 12:
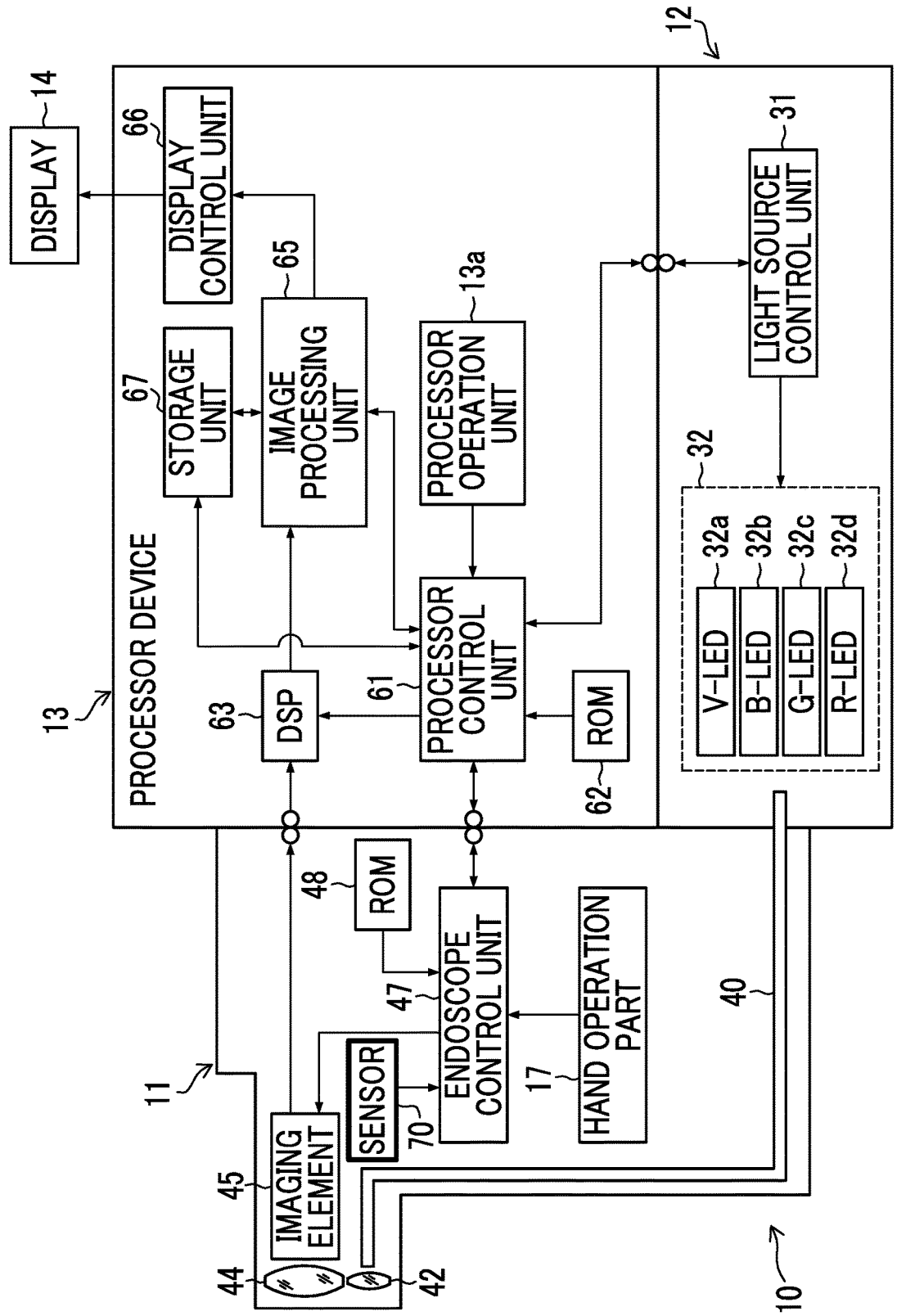
FIG. 12 is a block diagram illustrating an electric configuration of the endoscope device.

FIG. 12 is a block diagram illustrating an electric configuration of the endoscope device 10 of the embodiment. The parts already described in FIG. 2 are denoted by the same reference numerals, and the description thereof will be omitted.

In the endoscope device 10 of the embodiment, the endoscope scope 11 comprises the sensor 70. It is sufficient that the sensor 70 is provided at an appropriate location in the endoscope scope 11, and the sensor 70 is provided at the bendable portion 16*b* or the insertion part-distal end portion 16*a*, for example. Further, in the endoscope scope 11, a single sensor 70 may be provided or a plurality of sensors 70 may be provided. Here, as a specific example of the sensor 70, at least one of an acceleration sensor, a gyro sensor, a magnetic field sensor, a bend sensor, an infrared sensor, or an ultrasonic sensor is adopted.

Figure 13:
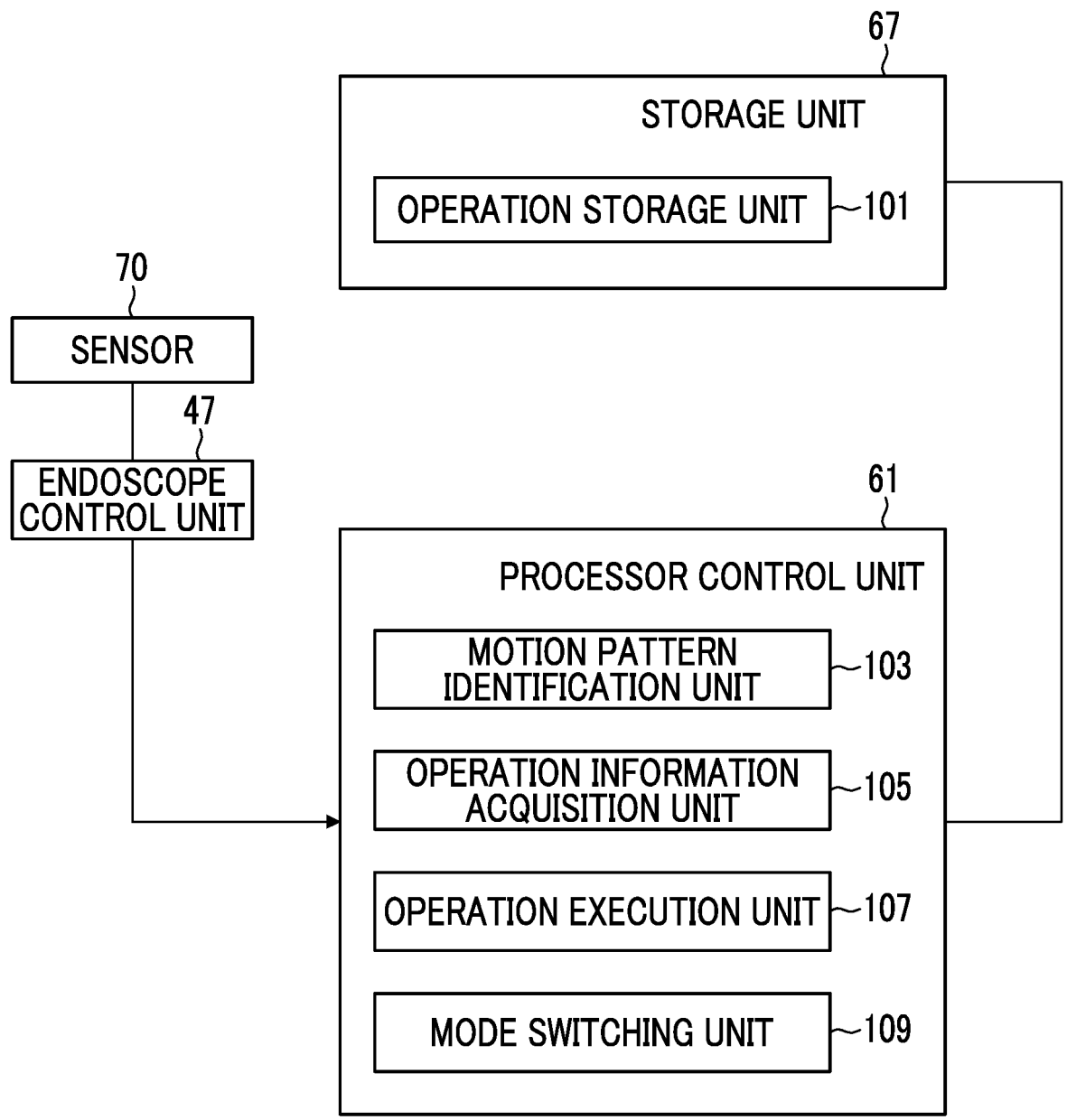
FIG. 13 is a block diagram illustrating a functional configuration example.

FIG. 13 is a block diagram illustrating a main functional configuration example of the second embodiment. The parts already described in FIG. 3 are denoted by the same reference numerals, and the description thereof will be omitted.

In the embodiment, the operation storage unit 101 is provided to the storage unit 67, and the motion pattern identification unit 103, the operation information acquisition unit 105, the operation execution unit 107, and the mode switching unit 109 are provided to the processor control unit 61. The sensor information output from the sensor 70 is input to the processor control unit 61 via the endoscope control unit 47.

The motion pattern identification unit 103 identifies the motion pattern of the scope head on the basis of the sensor information output from the sensor 70 included in the scope unit. The motion pattern identification unit 103 identifies the motion pattern of the scope head using a known technique.

Third Embodiment

Next, a third embodiment will be described. The motion pattern identification unit 103 of the embodiment identifies the motion pattern on the basis of the input operation information input by the operator via the hand operation part 17.

FIG. 14 is a block diagram illustrating a main functional configuration example of the third embodiment. The parts already described in FIG. 3 are denoted by the same reference numerals, and the description thereof will be omitted.

In the embodiment, the operation storage unit 101 is provided to the storage unit 67, and the motion pattern identification unit 103, the operation information acquisition unit 105, the operation execution unit 107, and the mode switching unit 109 are provided to the processor control unit 61. The input operation information which is input via the hand operation part 17 on the basis of the operator's operation is input to the processor control unit 61 through the endoscope control unit 47.

The motion pattern identification unit 103 identifies the motion pattern of the scope head on the basis of the input operation information input through the operator operating the hand operation part 17. For example, the operator operates the angle knob 21 of the hand operation part 17 so that the input operation information is input, and the motion pattern identification unit 103 identifies the motion pattern of the scope head on the basis of the input operation information. Here, the input operation information analyzed by the motion pattern identification unit 103 is information for operating respective mechanisms to move the scope head, and is information by which the movement of the scope head can be specified by analyzing the input operation information. Further, by attaching a rotation angle sensor or the like to the angle knob 21 and detecting the angle of the angle knob 21 using the rotation angle sensor, the motion pattern of the scope head may be identified on the basis of the detected rotation angle.

<Other Examples of Motion of Scope Head>

As the motion pattern of the scope head, various specific movements of the scope head can be adopted. For example, as the variations of the direction for moving the scope head, "vertically shaking", "horizontally shaking", "rotating", and "moving forward and backward" are considered. Further, the motion pattern that may not be performed during the normal observation is distinguished from a normal motion based on the number of motions (shaking three times or the like) or the speed of the motion (quickly shaking or the like). As a specific example of a quick movement, the reciprocation is performed once in the same direction at a rotation speed of 180 [degree/second] or higher. In addition, as the number of repetitions of the same motion, three times of reciprocation in the same direction within one second is considered. Further, a plurality of operations may be combined, and specific examples thereof include the reciprocation is performed once in one direction at a speed of 90 [degree/second] or higher while pressing a button (light source switching or the like). As described above, the motion pattern may include not only the movement of the scope head but also at least one piece of information on the number of times or speed of the specific movement of the scope head.

The examples of the invention have been described above, but the invention is not limited to the above-described embodiments and can be variously modified without departing from the spirit of the invention.

EXPLANATION OF REFERENCES

10: endoscope device
11: endoscope scope
12: light source device
12a: light source operation unit
13: processor device
13a: processor operation unit
14: display
16: insertion part
16a: insertion part-distal end portion
16b: bendable portion
16c: flexible tube portion
17: hand operation part
18: universal cord
21: angle knob
22: operation button
23: forceps inlet
25a: connector part
25b: connector part
31: light source control unit
32: light source unit
32a: V-LED
32b: B-LED
32c: G-LED
32d: R-LED
40: light guide
42: illumination lens
44: objective lens
45: imaging element
47: endoscope control unit
48: ROM
61: processor control unit
62: ROM
65: image processing unit
66: display control unit
67: storage unit
70: sensor
101: operation storage unit
103: motion pattern identification unit
105: operation information acquisition unit
107: operation execution unit
109: mode switching unit

What is claimed is:

1. An endoscope device comprising:
a processor; and
a memory, wherein:
the processor identifies a single or plurality of motion patterns indicating a specific movement of a scope head of a scope;
the memory stores a single or plurality of pieces of operation information for instructing an operation of the endoscope device, and the single or plurality of motion patterns of the scope head in association with each other;

the processor acquires the operation information corresponding to the motion pattern from the memory on the basis of the identified motion pattern indicating the specific movement of the scope head of the scope; and the processor executes an operation corresponding to the acquired operation information.

2. The endoscope device according to claim 1,
wherein the processor identifies the motion pattern on the basis of time-series images acquired by an image sensor included in the scope head.

3. The endoscope device according to claim 2,
wherein the processor calculates a movement vector in the time-series images, and identifies the motion pattern of the scope head on the basis of the movement vector.

4. The endoscope device according to claim 1,
wherein the processor identifies the motion pattern of the scope head on the basis of sensor information output from a sensor included in the scope.

5. The endoscope device according to claim 4,
wherein the scope includes at least one of an acceleration sensor, a gyro sensor, a magnetic field sensor, a bend sensor, an infrared sensor, or an ultrasonic sensor.

6. The endoscope device according to claim 1,
wherein the processor identifies the motion pattern on the basis of input operation information that is input via a handle of the scope.

7. The endoscope device according to claim 1, wherein the processor is further configured to:
switch between a scope head motion input mode in which the operation is executed, and a normal observation mode in which the operation is not executed.

8. The endoscope device according to claim 7,
wherein the memory stores the operation information for instructing a mode switching operation, and the single or plurality of motion patterns of the scope head in association with each other.

9. The endoscope device according to claim 1,
wherein the memory stores the operation information regarding an adjustment operation for observation conditions and the single or plurality of motion patterns in association with each other.

10. The endoscope device according to claim 1,
wherein the memory stores an input operation for approval or disapproval and the single or plurality of motion patterns of the scope head in association with each other.

11. The endoscope device according to claim 10,
wherein the memory stores a bending motion of the scope head in a vertical direction in association with the input operation for approval, and stores a bending motion of the scope head in a horizontal direction in association with the input operation for disapproval.

12. The endoscope device according to claim 1,
wherein the motion pattern includes at least one piece of information on the number of times or speed of the specific movement of the scope head.

13. An endoscope operation method comprising:
identifying a single or plurality of motion patterns indicating a specific movement of a scope head of a scope;
acquiring, from a memory, which stores a single or plurality of pieces of operation information for instructing an operation of an endoscope device and the single or plurality of motion patterns of the scope head in association with each other, the operation information corresponding to the motion pattern on the basis of the identified motion pattern indicating the specific movement of the scope head of the scope; and
executing an operation corresponding to the acquired operation information.

14. A non-transitory computer readable recording medium causing a computer to execute, in a case where a command stored in the recording medium is read by the computer, an endoscope operation method comprising:
identifying a single or plurality of motion patterns indicating a specific movement of a scope head of a scope;
acquiring, from a memory, which stores a single or plurality of pieces of operation information for instructing an operation of an endoscope device and the single or plurality of motion patterns of the scope head in association with each other, the operation information corresponding to the motion pattern on the basis of the identified motion pattern indicating the specific movement of the scope head of the scope; and
executing an operation corresponding to the acquired operation information.

15. The endoscope device according to claim 1,
wherein the memory stores an input operation for either approval or disapproval regarding a lesion detection result and the single or plurality of motion patterns of the scope head in association with each other.

* * * * *